(12) United States Patent
Ma et al.

(10) Patent No.: US 9,861,288 B2
(45) Date of Patent: Jan. 9, 2018

(54) TRANSPARENT AND FLEXIBLE NEURAL ELECTRODE ARRAYS

(71) Applicant: Wisconsin Alumni Research Foundation, Madison, WI (US)

(72) Inventors: Zhenqiang Ma, Middleton, WI (US); Justin Cole Williams, Deerfield, WI (US); Dong-Wook Park, Madison, WI (US); Amelia Ann Schendel, Andover, MN (US); Solomon Tadesse Mikael, Silver Spring, MD (US)

(73) Assignee: Wisconsin Alumni Research Foundation, Madison, WI (US)

( * ) Notice: Subject to any disclaimer, the term of this patent is extended or adjusted under 35 U.S.C. 154(b) by 319 days.

(21) Appl. No.: 14/329,067

(22) Filed: Jul. 11, 2014

(65) Prior Publication Data

US 2016/0007874 A1    Jan. 14, 2016

(51) Int. Cl.
*A61B 5/0478*    (2006.01)
*A61B 5/04*    (2006.01)
*A61B 5/00*    (2006.01)

(52) U.S. Cl.
CPC ........ *A61B 5/04001* (2013.01); *A61B 5/0478* (2013.01); *A61B 5/6868* (2013.01); *A61B 2503/40* (2013.01); *A61B 2503/42* (2013.01); *A61B 2562/046* (2013.01); *A61B 2562/125* (2013.01)

(58) Field of Classification Search
CPC .................................................. A61B 5/04001
USPC ................................................. 600/377, 378
See application file for complete search history.

(56) References Cited

U.S. PATENT DOCUMENTS

| | | | | |
|---|---|---|---|---|
| 6,024,702 A | * | 2/2000 | Iversen ................ | A61B 5/0422 600/378 |
| 6,330,466 B1 | * | 12/2001 | Hofmann ........... | A61B 5/04001 600/378 |
| 6,834,200 B2 | * | 12/2004 | Moxon .............. | A61B 5/04001 600/373 |
| 7,689,260 B2 | * | 3/2010 | Finch ................... | A61N 1/0529 600/378 |
| 7,774,053 B2 | | 8/2010 | Garell et al. | |
| 8,386,007 B2 | | 2/2013 | Williams et al. | |

(Continued)

FOREIGN PATENT DOCUMENTS

WO    WO2009003025    12/2008
WO    WO2013010161    1/2013

(Continued)

OTHER PUBLICATIONS

Blau et al., Flexible, all-polymer microelectrode arrays for the capture of cardiac and neuronal signals, Biomaterials, vol. 32, Dec. 9, 2010, pp. 1778-1786.

(Continued)

*Primary Examiner* — Lee S Cohen
(74) *Attorney, Agent, or Firm* — Bell & Manning, LLC

(57) ABSTRACT

Devices for detecting electrical activity in electrically active biological tissues and methods for using the devices are provided. The devices include an electrode array that is configured for implantation on electrically active biological tissue. The electrode array comprises a plurality of electrode sites comprising one or more layers of transparent, electrically conductive graphene disposed on a transparent substrate.

20 Claims, 11 Drawing Sheets

(56) References Cited

U.S. PATENT DOCUMENTS

| | | | |
|---|---|---|---|
| 8,948,840 B2* | 2/2015 | Guimera Brunet | A61B 5/053 600/383 |
| 2011/0087126 A1 | 4/2011 | Zorzos et al. | |
| 2013/0085359 A1 | 4/2013 | Yao et al. | |
| 2013/0090542 A1 | 4/2013 | Kipke et al. | |
| 2013/0144365 A1 | 6/2013 | Kipke et al. | |
| 2014/0067023 A1* | 3/2014 | Register | A61L 31/02 607/89 |
| 2016/0038755 A1* | 2/2016 | Lundmark | A61N 1/0551 607/92 |

FOREIGN PATENT DOCUMENTS

| | | |
|---|---|---|
| WO | WO2013116811 | 8/2013 |
| WO | WO2015/153958 | * 10/2015 |

OTHER PUBLICATIONS

Kim et al., Large-scale pattern growth of graphene films for stretchable transparent electrodes, Letters, vol. 457, Feb. 5, 2009, pp. 706-710.

Kwon et al., Opto-µECoG Array: Transparent µECoG Electrode Array and Integrated LEDs for Optogenetics, Biomedical Circuits and Systems Conference (BioCAS), IEEE, Nov. 28, 2012.

Ledochowitsch et al., A Transparent µECoG Array for Simultaneous Recording and Optogenetic Stimulation, Conf Proc IEEE Eng Med Biol Soc., Aug. 30, 2011, pp. 2937-2940.

Cardin et al., Targeted optogenetic stimulation and recording of neurons in vivo using cell-type-specific expression of Channelrhodopsin-2, Nature Protocols, vol. 5, No. 2, Jan. 21, 2010, pp. 247-254.

Srinivasan et al., Rapid volumetric angiography of cortical microvasculature with optical coherence tomography, Available online on or before Apr. 16, 2014.

* cited by examiner

TRANSPARENT AND FLEXIBLE NEURAL ELECTRODE ARRAYS

REFERENCE TO GOVERNMENT RIGHTS

This invention was made with government support under N00014-09-1-0803 awarded by the US Navy/ONR and N66001-12-C-4025 awarded by the US Navy. The government has certain rights in the invention.

BACKGROUND

Neural interfaces enable a connection between nervous tissue and the ex vivo environment. These devices are not only useful for neuroscience research, but also provide therapy for patients afflicted with a multitude of neuronal disorders. The advent of optogenetics, a new technique involving genetic modification of neural cells to make them susceptible to light stimulation, has not only revolutionized neuroscience research, but also transformed the requirements for neural interfacing devices. It is now desired to optogenetically stimulate the cortex with light while simultaneously recording the evoked response. Neural surface electrode arrays, such as micro-electrocorticography (micro-ECoG) devices, strike a balance between invasiveness and recorded signal quality. However, these devices use opaque metallic conductive materials. Thus, it is possible to stimulate around the electrode sites, but not directly at the electrode-tissue interface. Additional advancements in in vivo imaging modalities could provide valuable information regarding the tissue response to implanted electrode arrays, and help correlate tissue behavior with recorded signals. To date, however, these methods have mainly been used to image tissue surrounding micro-ECoG electrode sites, since imaging at the electrode-tissue interface is infeasible, due to the conductor opacity.

Transparent micro-ECoG arrays have been fabricated using indium-tin oxide (ITO), a transparent conductor commonly used in solar cells. ITO, however, is not ideal for employment with micro-ECoG technology, for a variety of reasons. ITO is brittle and requires high-temperature processing not suitable for use with the low-glass-transition-temperature polymer substrates. In addition, ITO has process-dependent transparency, which is rather limited in the ultraviolet (UV) and infrared (IR) wavelength ranges that are used for stimulating various opsin types and visualizing fluorescently tagged cells in neural imaging and optogenetic applications.

SUMMARY

Devices for detecting electrical activity in electrically active biological tissues and methods for using the devices are provided. In some embodiments, the devices are electrophysiology devices, such as electrocorticography devices, that record neural signals generated in nervous tissue.

One embodiment of the devices includes a micro-electrode array that comprises: a biocompatible, dielectric substrate; a plurality of electrode sites on the biocompatible, dielectric substrate, the electrode sites comprising one or more sheets of electrically conductive graphene; a plurality of electrically conductive contacts on the biocompatible, dielectric substrate; and electrically conductive interconnects connecting the neural electrode sites to the contacts. The electrode sites and the portion of the substrate on which the electrode sites are disposed are transparent in at least a portion of the wavelength range from about 300 to about 2000 nm and are configured for implantation on biological tissue.

One embodiment of a method of detecting electrical activity using a device of type described herein comprises: implanting the micro-electrode array on electrically active biological tissue; and recording an electrical response, such as an action potential, generated by the tissue at the electrode sites. For example, in the case of an electrocorticography device, an embodiment of a method of detecting neural signals using the electrocorticography device comprises: implanting the micro-electrode array on nervous tissue; and recording a neural response generated by neural cells in the nervous tissue at the electrode sites.

Other principal features and advantages of the invention will become apparent to those skilled in the art upon review of the following drawings, the detailed description, and the appended claims.

BRIEF DESCRIPTION OF THE DRAWINGS

Illustrative embodiments of the invention will hereafter be described with reference to the accompanying drawings, wherein like numerals denote like elements.

DETAILED DESCRIPTION

Electrophysiology devices and methods for using them to record electrical signals generated in electrically active biological tissue are provided. In some embodiments, the devices are micro-ECoG devices that record neural signals generated in brain tissue. The devices include an electrode array that is configured for implantation onto the surface of the tissue. This array comprises a plurality of electrode sites, which comprise one or more layers of transparent, electrically conductive graphene, disposed on a substrate. Both the substrate and the electrode sites are transparent over a broad wavelength spectrum. This transparency allows incident light to be passed through the electrode array onto the underlying tissue and further allows light from the underlying tissue to be passed through the electrode array for detection and/or imaging. As a result, the devices make it possible to optically stimulate and/or image tissue directly underlying the electrode array.

The devices can be used to detect signals in a variety of electrically active biological tissues, including neural tissue, muscle tissue and cardiac tissue. By way of illustration, the devices can be used to detect evoked neural signals from brain tissues, action potentials generated from muscle contractions or cardiac action potentials.

Figure 1:
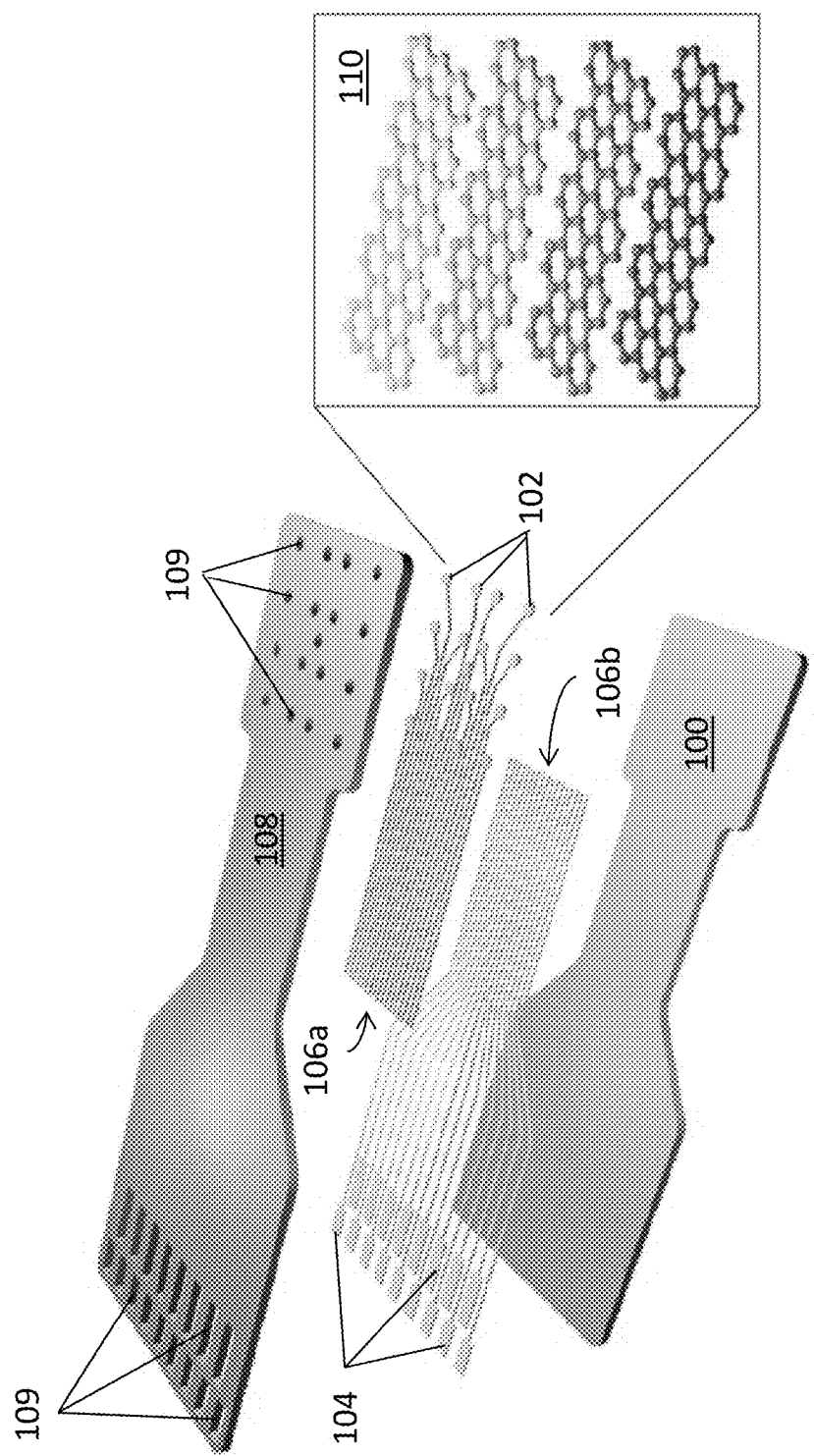
FIG. 1 is an exploded view of one embodiment of an electrophysiology device.
Figure 2:
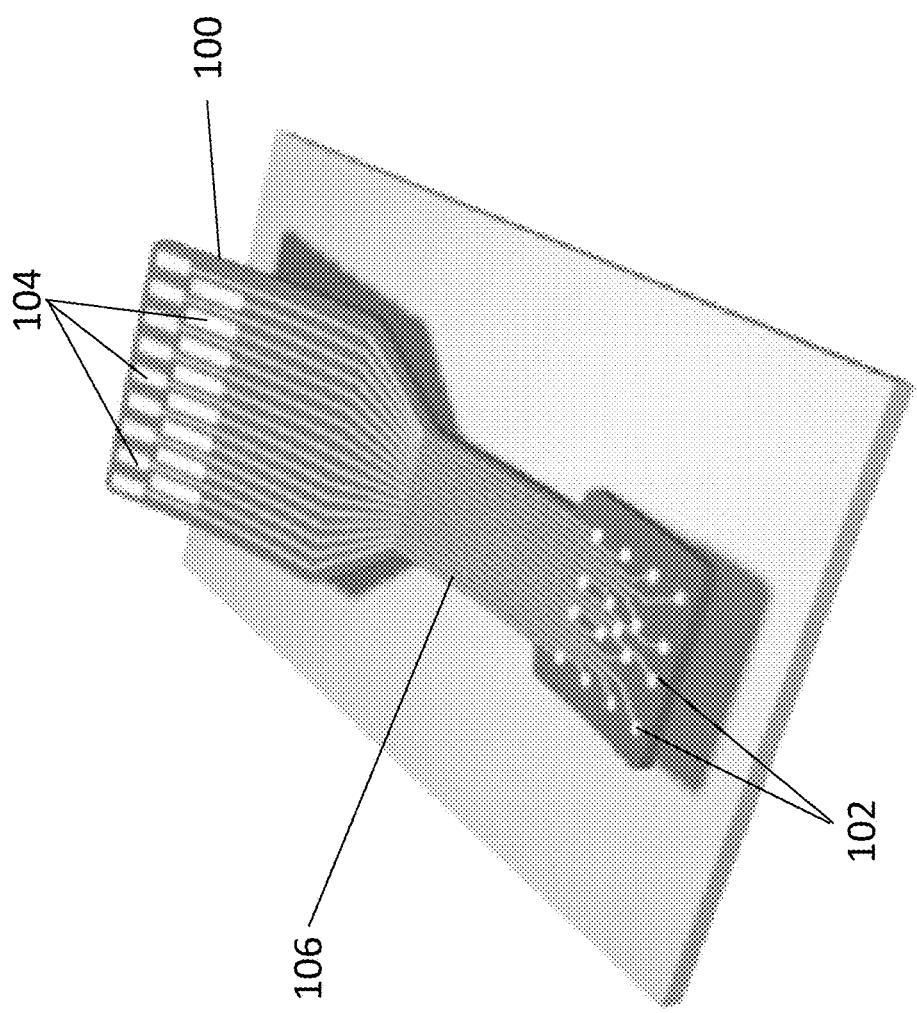
FIG. 2 is an intact view of the device of claim 1.

An exploded view of one embodiment of an electrophysiology device is illustrated schematically in FIG. 1. A diagram of the intact device is shown in FIG. 2. The device comprises a micro-electrode array composed of a substrate 100, a plurality of electrode sites 102 disposed on the surface of substrate 100, a plurality of electrically conductive contacts 104 disposed on the surface of substrate 100, electrically conductive interconnects 106 connecting electrode sites 102 to contacts 104, and an overlayer 108 disposed over at least some portions of interconnects 106a and 106b. The portion of the micro-electrode array comprising electrode sites 102 is configured to be implanted on electrically active biological tissue while the portion comprising contacts 104 is configured to be connected to an external device. Therefore, overlayer 108 defines apertures 109 over electrode sites 102 and contacts 104 so that the electrode sites can be exposed to the tissue of a subject and the contacts can be connected to an external device. The micro-electrode array can be considered configured for implantation on electrically active biological tissue if it lends itself, in terms of shape, dimensions and materials, to implantation in a practical manner without harming the tissue on which, or the subject in which, it is implanted.

Each electrode site comprises a single sheet of graphene or a stack of two or more graphene sheets 110. The graphene sheets are transparent over a broad range of wavelengths, including wavelengths in the ultraviolet (UV), visible (vis), and infrared (IR) regions of the electromagnetic spectrum. For the purposes of this disclosure, a material is considered to be transparent to light of a given wavelength if it has a transmission of at least 50% at that wavelength. This includes materials having a transmittance of at least 70%, at least 80% and at least 90%.

The number of graphene sheets present at the electrode sites will depend, at least in part, on the conductivity and transparency requirements of the intended application because a greater number of graphene sheets can provide a higher electrical conductivity, but may reduce the transparency of the electrode sites. Thus, in some embodiments the electrode sites have from one to ten graphene sheets. This includes embodiments in which the electrode sites have from two to six graphene sheets.

The graphene sheets at the electrode sites can have a planar configuration, as illustrated in FIG. 1. However, the sheets can also be used in a non-planar configuration. For example, wrinkled or crumpled graphene sheets can be used. Non-planar graphene provides an electrode site having a higher surface area than an electrode site comprising planar graphene. A higher surface area can provide an electrode site with increased electrical conductivity in solution. In some embodiments, one or more regions of the graphene are non-planar (e.g., wrinkled) while one or more other regions are planar. For example, an electrode site may be designed such that the graphene around the perimeter of the site is non-planar, while the graphene in the center region (i.e., the region surrounded by the perimeter) is planar.

Various methods for imparting a non-planar structure to the graphene sheets may be used. For example, the graphene sheets can be wrinkled by depositing a stressor material, such as non-stoichiometric silicon nitrides or silicon oxides ($SiN_x$ and $SiO_x$), onto the surface of the graphene sheet. These materials are characterized by built-in stress. When the stressor materials are deposited on the graphene, the graphene will wrinkle up by complying with the built-in stress of the stressor materials. If the stressor materials are patterned into special planar forms, the graphene wrinkles into pre-defined patterns. The magnitude of the wrinkles will depend on the stressor materials, their built-in stress and patterning forms, which further depend on the stoichiometry and the deposition temperature. A method for fabricating wrinkled graphene using a stressor material is illustrated in Example 2.

The substrate is formed from a transparent, biocompatible, dielectric material. By 'biocompatible' it is meant that the material is not harmful to or does not induce scarring of nearby tissue, or does not degrade in terms of its intended function in the properties of living tissue on which it is to be implanted. The entire substrate may be a transparent and biocompatible. However, for many applications, only the portion of the substrate on which the electrode sites are disposed (i.e., the portion of the micro-electrode array that is configured to be implanted on the biological tissue) need be transparent and biocompatible. Thus, the substrate may comprise a transparent, biocompatible portion underlying the electrode sites and a non-transparent and/or non-biocompatible portion underlying the electrically conductive interconnects and/or contacts. The substrate is also desirably mechanically flexible, such that is able to conform to the tissue (e.g., the surface of a cerebral cortex) without cracking, splitting or otherwise damaging the device.

The overlayer protects and isolates the electrically conductive interconnects. Like the substrate, the overlayer comprises a transparent, biocompatible, dielectric material and is desirably mechanically flexible. The overlayer may be, but is not necessarily, made from the same material as the substrate. The graphene at the electrode sites is exposed through apertures in the overlayer. However, the material of the overlayer may overlap with at least a portion of the perimeter of the graphene layer or layers in order to prevent the graphene from delaminating from the substrate in solution. Transparent, biocompatible polymers are examples of materials from which the substrate and overlayer can be formed. The polymers should be selected such that they are transparent over a broad range of wavelengths, including wavelengths in the UV, visible and IR regions of the electromagnetic spectrum.

The transparency of the devices at and around an electrode site will reflect the combined transparencies of the graphene, the substrate material and the overlayer material. By way of illustration, in some embodiments the graphene, the substrate, the overlayer (if present) and the electrode sites are transparent over at least a portion of the wavelength range from about 300 to about 2000 nm. This includes embodiments in which the graphene, the substrate, the overlayer (if present) and the electrode sites are transparent over at least a portion of the wavelength range from about 400 to about 1800 nm. However, depending on the intended application of the device, a smaller transparency range may be acceptable. For example, for electrophysiology recordings that use optical stimulation, it may be sufficient that the electrode site is transparent over the wavelength range of the stimulating light. Similarly, for electrophysiology recordings conducted in conjunction with tissue imaging (e.g., fluorescence or optical coherence tomography), it may be sufficient that the electrode sites are transparent over the wavelength range of the incident and imaged light. By way of illustration, in some embodiments the graphene, the substrate, the overlayer (if present) and the electrode sites are transparent over at least a portion of one or more of the UV, visible and IR regions of the electromagnetic spectrum, but are non-transparent over at least a portion of one or more of the UV, visible and IR regions of the electromagnetic spectrum.

Examples of polymers that may be used as substrate and overlayer materials include parylene, polydimethysiloxane (PDMS), polyester (PET), polyimide (PI), polyethylene napthalate (PEN), polyetherimide (PEI), along with fluoropolymers (FEP) and copolymers thereof. In some embodiments, the substrate and overlayer are formed from a shape memory polymer—that is, a polymer that undergoes a planar to non-planar transformation in response to a change in temperature. For example, a shape memory polymer may adopt a planar configuration at room temperature (~23° C.), but a non-planar configuration at the body temperature of a subject into which the micro-electrode array is implanted. Examples of transparent, biocompatible, dielectric shape memory polymers are described in T. Ware, D. Simon, R. L. Rennaker, W. Voit, Smart Polymers for Neural Interfaces, *Polymer Reviews* 53 (1), 108-129 and Xie T. Recent advances in polymer shape memory. *Polym.* 2011; 52:4985-5000, the disclosures of which, as they relate to shape memory polymers, are incorporated herein by reference.

The substrate and overlayer should be sufficiently thin to provide a mechanically flexibility device with adequate transparency. By way of illustration, some embodiments of the devices have a thickness of no greater than about 100 μm. This includes devices having a thickness of no greater than about 50 μm and further includes devices having a thickness of no greater than about 20 μm.

The electrically conductive contacts are provided so that the micro-electrode arrays can be electrically connected to external devices, such as devices that are configured to receive the signals recorded at the electrode sites and to amplify, display, store and/or analyze those signals. The electrically conductive interconnects provide electrical connections between the electrode sites and the contacts and may comprise, for example, wires and/or traces. The contacts and interconnects can be metal contacts and interconnects, but can also be formed from other electrically conductive materials. The interconnects located on the portion of the micro-electrode array that is configured to contact the electrically active tissue are desirably transparent. Therefore, as shown in FIG. 1, the interconnects can comprise a transparent portion 106a and a non-transparent portion 106b. For example, transparent portions 106a may comprise transparent, electrically conductive graphene and non-transparent portions 106b can comprises a metal, such as gold. The transparent and non-transparent portions of each interconnect overlap along their length in order to form a continuous connection.

Figure 3:
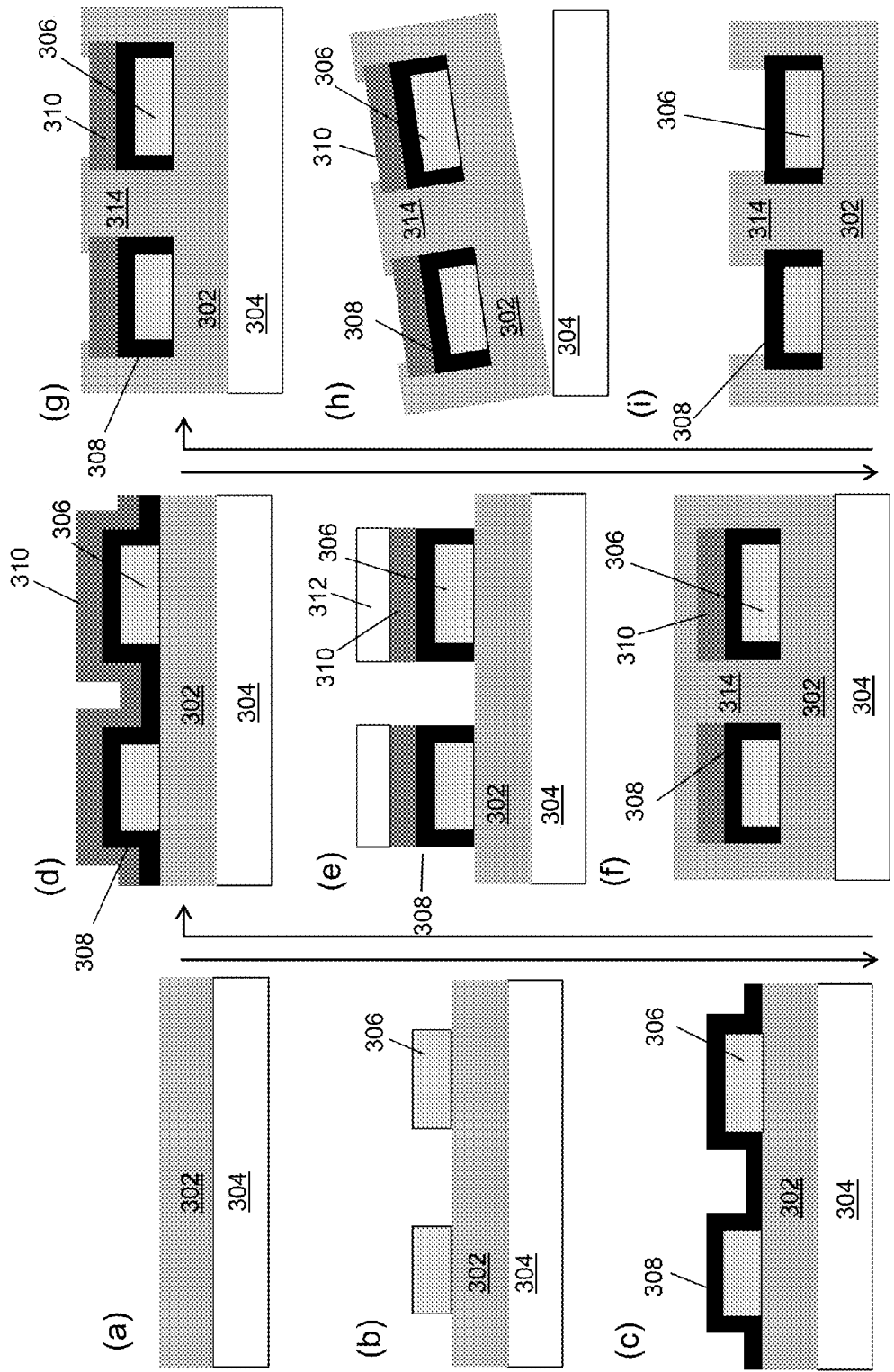
FIG. 3 is a schematic diagram of one embodiment of a method for fabricating an electrophysiology device.

A method of fabricating a micro-electrode array is illustrated schematically in FIG. 3. That figure provides a cross-sectional view taken through the end of the device that is configured to be connected to an external device and, therefore, includes the metal contacts. First a layer of a dielectric, biocompatible, transparent material 302 is formed on a support substrate 304 (panel (a)). Electrically conductive contacts 306 and interconnects are then patterned over layer 302 (panel (b)). One or more sheets of graphene 308 are then transferred onto layer 302 and contacts 306 (panel (c)). To protect the graphene from possible damage during subsequent process steps, protective layer 310 is then deposited over the structure (panel (d)). Protective layer 310 and graphene layer 308 are then patterned and etched to form interconnections and electrode sites using an etch mask (panel (e)). The etch mask is then removed and overlayer 314 is deposited between contacts 306 and over the structure (panel (f)). A portion of overlayer 314 over each contact 306 is removed to expose the underlying contact (panel (g)). Next, the device is released from support substrate 304 (panel (h)) and protective layer 310 removed.

The devices can be used to record electrical activity (e.g., action potentials) in vivo by implanting the micro-electrode array on the electrically active tissue of a subject and recording evoked electrical signals. The tissue on which the micro-electrode arrays are implanted may be at the surface of an organ or muscle or may be sub-surface tissue, as in the case of a penetrating implantable micro-electrode array. For example, the devices can be used to record neural signals in vivo by implanting the micro-electrode array on the nervous tissue of a subject and recording evoked neural signals. In this application, the micro-electrode array may be implanted onto a cerebral cortex and action potentials generated by neural cells can be recorded at the electrode sites. The subject may be an animal, such as a mammal, including a human. The recorded signals may be evoked by sensory stimuli that is generated internally or by an external source. In some embodiments the evoked signals are generated in response to an electrical stimulus, such as the application of an electrical current to the subject. In other embodiments, the evoked signals are generated in response to an optical stimulus.

Optogenetics is an example of a technique that employs optical stimulation to evoke a neural response. Optogenetics uses biological cells that have been modified to incorporate light-sensitive proteins, such as channelrhodopsin and halorhodopsin, into their cell membranes. These proteins act as light-activated ion channels, allowing the flow of specific ions into and out of the cell when subjected to light having particular wavelengths. Depending on the type of ion channel, the ion diffusion will either cause a depolarization or a hyperpolarization of the cell, which, in the case of neurons, causes excitation or inhibition of neural activity, respectively. When the light-sensitized cells are exposed to incident light of the appropriate wavelength, optically evoked neural signals are generated. The appropriate wavelength range will depend on the particular light-sensitive protein that is used. However, typically, incident light having wavelengths in the UV or visible range is employed. Suitable light sources for generating the incident light may comprise light-emitting sources, waveguides and/or spatial light modulators. These include lasers, light-emitting diodes, and fiber optics. When the electrophysiology devices are used in optogenetic techniques, the incident light can be directed onto the surface of the nervous tissue through the transparent electrode sites that are used to record the resulting response.

In addition, because the micro-electrode arrays are transparent, the tissue underlying the electrode sites can be imaged while the micro-electrode array is in place and even while it is taking electrophysiological recordings. Images of the tissue are obtained by directing incident light onto the tissue, through the transparent electrode sites, and recording light returned from the tissue and transmitted through the transparent electrode sites. The returned light may be light that is reflected (e.g., backscattered) by the tissue or emitted by the tissue in response to the incident light. Fluorescence microscopy and optical coherence tomography (OCT) are two examples of imaging techniques that can be used in conjunction with electrophysiology.

In fluorescence microscopy, the tissue is labeled with fluorescent biomarkers. This can be accomplished, for example, by injecting a fluorophore-labeled probe into blood vessels that run through the tissue. Incident light having wavelengths suitable to induce the fluorophores to fluoresce is then directed onto the tissue and the resulting fluorescence is recorded by a photodetector, such as a fluorescence microscope. The optimal wavelengths for the incident light will depend on the specific fluorophore, and on the excitation process. Typically incident wavelengths include those in the range from about 400 nm to about 1800 nm. A description of an illustrative method for obtaining images of blood flow in brain tissue via fluorescence microscopy can be found in Schendel, A. A. et al. A cranial window imaging method for monitoring vascular growth around chronically implanted micro-ECoG devices. *J. Neurosci. Methods* 218, 121-130 (2013).

In OCT, imaging is performed by measuring the echo time delay and intensity of light backscattered from tissues. As such, OCT images represent differences in optical backscattering in a cross-sectional plane or volume of tissue. OCT imaging is conducted by directing a beam of incident light onto a tissue from which a portion of the light is backreflected from structures having different optical properties and from boundaries between different structures. Typically, the incident light is short pulsed light or continuous-wave short coherence length light with wavelengths in the infrared region of the electromagnetic spectrum with wavelengths in the range from about 700 nm to about 1 mm. The shapes and dimensions of the different structures in the tissue are determined by measuring the "echo" time it takes for light to be backreflected or backscattered at varying axial distances. A description of an illustrative method for obtaining OCT images of brain tissue can be found in Srinivasan, V. J. et al. Rapid volumetric angiography of cortical microvasculature with optical coherence tomography. *Opt. Lett.* 35, 43-45 (2010).

EXAMPLES

Example 1

This example illustrates the fabrication of a graphene-based, ultra flexible and conformal micro-electrocorticography array and demonstrates its versatile abilities through in vivo experiments. The devices are referred to as Carbon Layered Electrode Arrays (CLEAR) devices. The CLEAR devices, fabricated with graphene monolayers and implanted on the brain surface in rats and mice, were comprehensively evaluated and the results display the viability of these devices for neural electrophysiology applications. Optogenetic experiments, in vivo imaging of the cortical vasculature via fluorescence microscopy, and optical coherence tomography reveal additional unique abilities of these devices, made possible by their broad spectrum transparency.

Methods:

Graphene Growth and Transfer.

Graphene monolayers were grown on both sides of 2×3 cm sheets of copper (Cu) foil. The graphene on one side of the foil was etched using oxygen ($O_2$) plasma (50 W, 10 sccm $O_2$, 10 mTorr, for 1 minute). The remaining graphene was coated by 950k PMMA (polymethyl methacrylate) C4 (MicroChem) for protection of the monolayer graphene during subsequent process steps. Next, the copper foil was etched away in 0.25 M ferric chloride ($FeCl_3$) for 3 hours and the sample was then rinsed in de-ionized (DI) water. After copper etching, the graphene/PMMA was cleaned in 1:10 hydrofluoric (HF) acid for 1 hour to remove any copper composite residues and then rinsed in DI water.

The first graphene transfer was then performed on the desired substrate. After drying the PMMA/graphene sample in a $N_2$ atmosphere dry box, the PMMA was removed using acetone and the sample was rinsed in DI water. Following the above procedure, the graphene stacking was performed on the previously graphene-transferred substrate. Multiple layers of graphene could be stacked on the desired substrate using this method.

Wetting Property Control of Parylene C.

To transfer the graphene sheet to a parylene C coated silicon wafer substrate, it was desirable for the substrate surface to be hydrophilic so that the graphene could adhere easily and uniformly. To transform the intrinsically hydrophobic surface of parylene C to hydrophilic, two methods were tested: (1) thin $SiO_2$ layer deposition; and (2) Oxygen ($O_2$) plasma treatment, as described in Song, J. S., Lee, S., Jung, S. H., Cha, G. C. & Mun. M. S. Improved Biocompatibility of Parylene-C Films Prepared by Chemical Vapor Deposition and the Subsequent Plasma Treatment. *Journal of Applied Polymer Science.* 112, 3677-3685 (2009). It was found that both plasma treatment and $SiO_2$ deposition allowed for sufficient wetting of the substrate surface. Since plasma treatment is a faster, simpler process, it was selected for use in this study.

Following plasma treatment of the substrate, the clean PMMA/graphene sample was dried in a nitrogen atmosphere dry box, and then transferred to the pre-patterned substrate. The PMMA was then removed using acetone and the sample was rinsed in DI water. After the transfer of the initial sheet, the above process was repeated, transferring additional monolayer sheets onto the same spot until a 4-monolayer thick stack of graphene sheets was made. The full CLEAR device fabrication process is diagrammed in FIG. 3.

Detailed Fabrication Process

Figure 4:
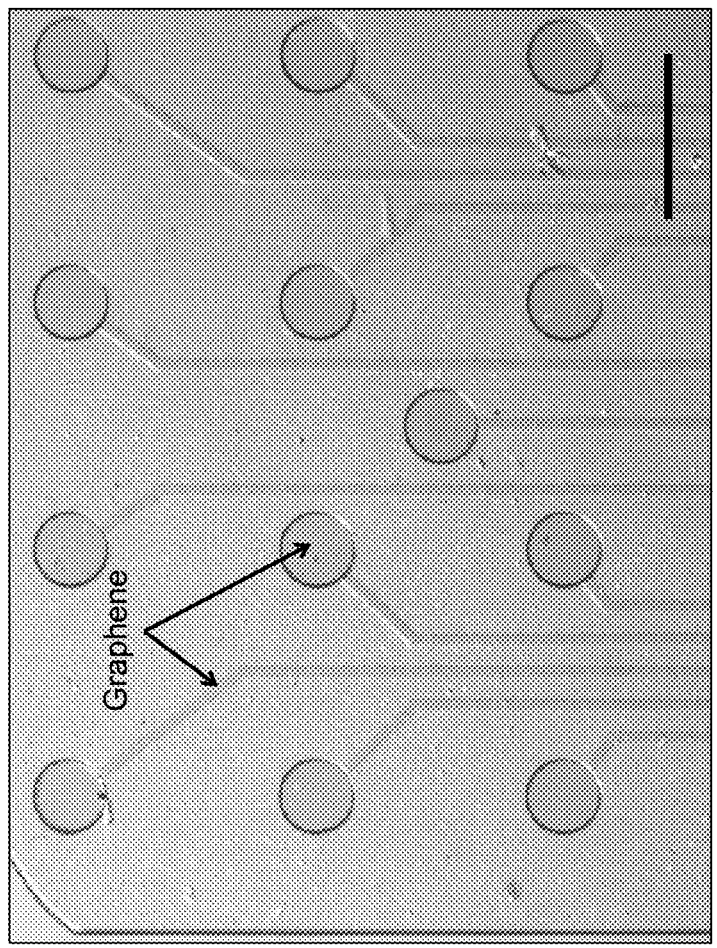
FIG. 4 is an image of the Carbon Layered Electrode Array ("CLEAR") electrophysiology device described in the example.

Parylene C (15 μm) was coated on a 4-inch silicon (Si) wafer using parylene deposition equipment (PDS 2010 Labcoter 2, Specialty Coating Systems Inc.). Interconnects and contacts were formed using Shipley 1813 photoresist and lift-off techniques. Gold (Au) metal 306 was used with a chromium (Cr) adhesion layer. For the CLEAR device, only the contacts and portions of the interconnects were patterned with metal, leaving the area of the device which would be in contact with the brain to be patterned with transparent graphene electrode sites and interconnects. Before graphene transfer, oxygen ($O_2$) plasma treatment was performed to transform the parylene C surface from hydrophobic to hydrophilic, as described above. Graphene was then transferred to the pre-patterned substrate using a wet transfer technique. To protect the graphene from possible damage during subsequent process steps, 30 nm $SiO_2$ was deposited using e-beam evaporation. Then the $SiO_2$/graphene layers were patterned using photolithography and dry etching. For the $SiO_2$ etch, reactive-ion etching (RIE) (Unaxis 790 dry etcher) was used with $CF_4$ gas at 45 sccm and $O_2$ gas at 5 sccm, 100 W power, and 40 mTorr pressure for 90 seconds. For the graphene etch, RIE with $O_2$ gas at 10 sccm, 50 W power, and 10 mTorr pressure was used for 60 seconds. After the photoresist was stripped, a second parylene C layer (10 μm) was evaporated for encapsulation. The parylene C was then patterned using two RIE steps with $O_2$ plasma. The first RIE step etched the device outline and the second RIE step etched outline, contacts and interconnects. Next, the wafer was soaked to release the devices from the silicon substrate. Finally, the $SiO_2$ protection layer was etched using 1:6 buffered oxide etchant (BOE) for 60 seconds, and the devices were rinsed thoroughly with DI water. FIG. 4 is an image of the device. The scale bar represents 500 μm.

Graphene Characterization Using Raman Spectroscopy.

The mono-layer graphene and multi-layer graphene samples were characterized using Raman spectroscopy and current-voltage (I-V) measurement on a $SiO_2$/Si substrate. The intensity ratio change of the 2D and G peaks for 1, 2, and 3-layer graphene verified the viability of the graphene stacking process, showing the unique phonon characteristics of graphene layers. The single sharp G peak is characteristic of the two-dimensional $sp^2$ bonded carbon atoms of graphene. For the 1 layer graphene, the G peak was located at 1572.5 $cm^{-1}$, and for the 3-layer graphene, the G peak was at 1563.3 $cm^{-1}$. Therefore, as the number of graphene layers increased, the G peak showed a left shift (redshift). The 2D peaks were at 2633 $cm^{-1}$ for the 1 layer graphene and at 2640.7 $cm^{-1}$ for 3-layer graphene, showing that the 2D peak experienced a right shift (blueshift) with increasing graphene layers. These peak shift trends are consistent with the previous Raman study for multilayer graphene. (See, Ferrari, A. C. et al. Raman Spectrum of Graphene and Graphene Layers. *Phys. Rev. Lett.* 97, 187401 (2006) and Ferrari, A. C. Raman spectroscopy of graphene and graphite: Disorder, electron-phonon coupling, doping and nonadiabatic effects. *Solid State Commun.* 143, 47-57 (2007).)

The 2D to G peak ratio ($I_{2D}/I_G$) trend demonstrated the changes occurring with the addition of each graphene layer. For the 1 layer graphene, the G peak intensity was the lowest, while the 2D peak intensity was the highest with $I_{2D}/I_G=3.63$. As the number of graphene layer was increased, the G peak intensity was increased and the 2D peak intensity was decreased, resulting in $I_{2D}/I_G$ ratios for 2-layer and 3-layer graphene were 1.43 and 0.91, respectively. This decreasing $I_{2D}/I_G$ ratio is characteristic of multilayer graphene samples. It is also important to note that the D peak near 1350 $cm^{-1}$, which is generally a result of sample defects, was not significant for the graphene layers. This proves that the CVD graphene grown for this study did not have a significant number of defects before and after stacking.

Graphene Characterization Using Current-Voltage Measurement.

To verify the resistance reduction effect of the stacked multilayer graphene, current-voltage (I-V) measurements were performed. For comparison, 1, 2, and 3-layers of graphene were transferred on each $SiO_2$/Si substrate with the graphene and source/drain metal patterning graphene channels with a width and length of 40 μm and 2.3 μm, respectively. The measured current values for the 2-layer graphene samples were about 1.6 times larger than those of the 1-layer graphene samples, while the 3-layer graphene sample showed about 1.85 times more current than the 1-layer graphene sheet. The resistance values extracted from the data indicate that the 2-layer and the 3-layer graphene samples have 0.62 and 0.55 times smaller resistances than the monolayer graphene sheet, respectively.

The sheet resistance for the 3-layer stacked graphene sample was calculated to be ~608Ω/□ (=35Ω/(2.3 μm/40 μm)) using the equation:

$$\text{Sheet Resistance} = \frac{\text{Sample Resistance}}{\frac{L}{W}}$$

L: channel length; W: channel width

Note that the sheet resistance value obtained in this study was not from a four point probe method, and thus contains the contact resistance term. Although a lower sheet resistance is desired for electrode applications, it is better to have low and stable in vivo electrode site impedance for micro-ECoG applications.

Surgical Implantation:

The complete surgical implantation procedure has been described previously. (See, Richner, T. J. et al. Optogenetic micro-electrocorticography for modulating and localizing cerebral cortex activity. *J. Neural Eng.* 11, 016010 (2014) and Schendel, A. A. et al. A cranial window imaging method for monitoring vascular growth around chronically implanted micro-ECoG devices. *J. Neurosci. Methods* 218, 121-130 (2013).) Briefly, after receiving pre-operative injections of buprenorphine (for pain management) and dexamethasone (to prevent brain swelling), animals were anesthetized with isoflurane gas and their heads immobilized. Incisions were made over the top of the skull and craniotomies were made with a surgical drill. Electrodes were stereotactically placed on the surface of the brain, over the somatosensory cortex, and circular glass coverslips were applied over the top of the array, forming the cranial window. The edges of the coverslips were sealed to the skull using dental acrylic. Ground and reference wires were attached to stainless steel screws, drilled into (rats) or glued to (mice) the skull. After everything was in place, the exposed screws were covered with dental acrylic to form a smooth cephalic implant. The skin was then sutured around the implant and the animals were revived. Animals received injections of buprenorphine post-surgery, as well as ampicillin antibiotic for one week following the implantation.

Electrical Evoked Potentials:

Animals were anesthetized with dexmedetomidine hydrochloride (0.05 mg/kg, Orion Pharma), and their hindlimbs shaved. Two adhesive surface electrodes were attached to one leg at a time and held in place with tape. These electrodes were hooked up to a stimulation box (A-M Systems Isolated Pulse Stimulator, Model 2100) linked to the TDT RZ2 system via a BNC cable. The animal's electrodes were plugged into the RZ2 system via the TDT headstage and PZ2 amplifier. In this way, an electrical stimulus was sent to the animal's sciatic nerve from the RZ2 system, and the response in the somatosensory cortex was recorded through the CLEAR device and sent back to the computer. After completion, the animals were revived with an injection of atipamezole hydrochloride (0.3 mg/kg, Orion Pharma).

In Vivo Imaging:

A full description of the in vivo vascular imaging procedure has been reported previously. (See, Schendel, A. A. et al. A cranial window imaging method for monitoring vascular growth around chronically implanted micro-ECoG devices. *J. Neurosci. Methods* 218, 121-130 (2013).) Imaging took place on a Leica MZ 16F stereoscope. Animals were anesthetized with a combination of isoflurane gas and dexmedetomidine, and kept on a heated water blanket. The animals' heads were stabilized to prevent breathing artifacts. Animals were injected with 12 mg/ml fluoresceine-isothiocyanate labeled dextran dissolved in phosphate-buffered saline to make the blood vessels fluorescent under blue light. Bright-field and fluorescent images were taken of the electrode arrays and surrounding brain tissue. Additionally, blood flow video recordings were acquired.

Optical Coherence Tomography:

Angiograms were recorded by a homemade SD-OCT system equipped with a 200 nm wide infrared source with a central wavelength of 1300 nm and an output power of 10 mW. The system was designed to obtain 5 nm axial and 4 nm lateral resolution with a 10× telecentric lens. (See, Farid Atry et al. Hemodynamic Response of Cortical Tissue to Optogenetic Stimulation in Transgenic Mice. *IEEE Trans. Biomed. Eng. Rev.*)

To obtain the OCT angiogram, 10 OCT B-scans per cross section were recorded at 650 tissue cross sections. The cross-sectional angiogram at each position was then obtained by applying a phase sensitive angiography technique to the OCT data. (See, Farid Atry et al. Hemodynamic Response of Cortical Tissue to Optogenetic Stimulation in Transgenic Mice. *IEEE Trans. Biomed. Eng. Rev.*) After stacking all 650 cross-sectional angiograms to form the volume angiogram, a 3D blurring kernel was applied to reduce the noise, and then the 2D maximum intensity projection of the angiograms was obtained.

For blood velocity measurement, the tissue was scanned at 1500 A-scans per mm, at the rate of 40,000 A-scans per second. At each position the Doppler shift introduced by the moving particles was estimated by calculating the average power spectrum density of a signal consisting of 7 consecutive OCT signals at that position ($\omega_a$). Axial velocity at that depth was then calculated by $v=40000*\omega_a/2\pi*$ (See, Farid Atry et al. Hemodynamic Response of Cortical Tissue to Optogenetic Stimulation in Transgenic Mice. *IEEE Trans. Biomed. Eng. Rev.*)

Figure 5:
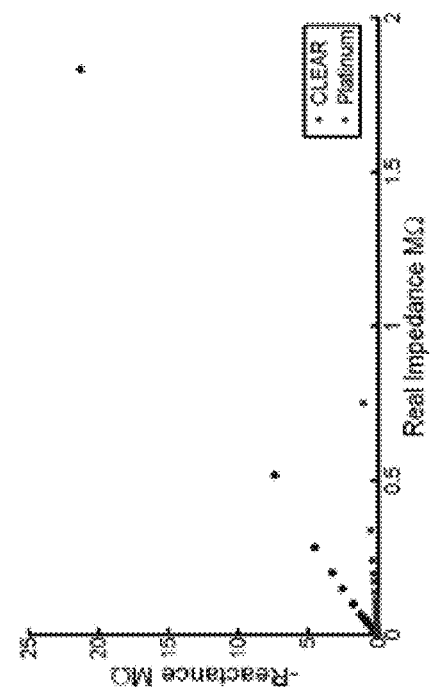
FIG. 5 is a graph of the electrical impedance spectra for the CLEAR device described in the example and a traditional platinum-based micro-ECoG device.

Results:

The patency of the completed devices was verified via electrical impedance spectroscopy. Impedance spectra were obtained for each electrode site using an Autolab PGSTAT12 potentiostat (Eco Chemie, Utrecht, Netherlands). Devices were connected to the Autolab machine via the PCB connectors, which were connected to a passive 32-channel Tucker-Davis Technologies (TDT) head stage. Impedances were evaluated at 30 different frequencies, ranging from 10 Hz to 30,937 Hz. If electrode sites had impedance values less than 600 kOhms at 1 kHz frequency, they were considered to be viable for implantation. 1 kHz frequency was selected for evaluation because it is known to be a common benchmark for neural impedance analysis. FIG. 5 shows representative electrical impedance spectra for CLEAR and traditional platinum micro-ECoG devices tested in saline. It is apparent from the plot that the phase angle is higher in the case of the CLEAR device. This means that the value of the reactance is higher for the graphene sites than for the platinum. However, the average magnitude of the impedance at 1 kHz frequency was only slightly higher for the CLEAR device than for the platinum array (243.5±5.9 k$\Omega$ for graphene vs. 188.8±92.9 k$\Omega$ for platinum). Since the signal recording apparatus involves the use of a high input impedance amplifier, the reactance difference is not expected to have adverse effects on the signal recordings.

Figure 6B:
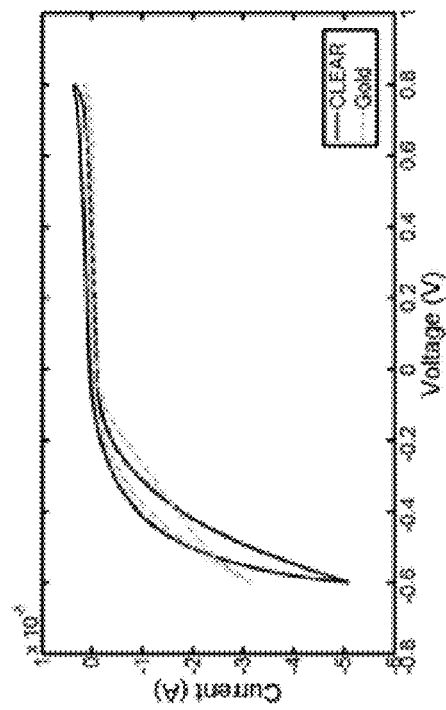
FIGS. 6A and 6B are graphs of the average current-voltage curves for a CLEAR device, a micro-ECoG device having gold electrode sites and a micro-ECoG device having platinum electrode sites.
Figure 6A:
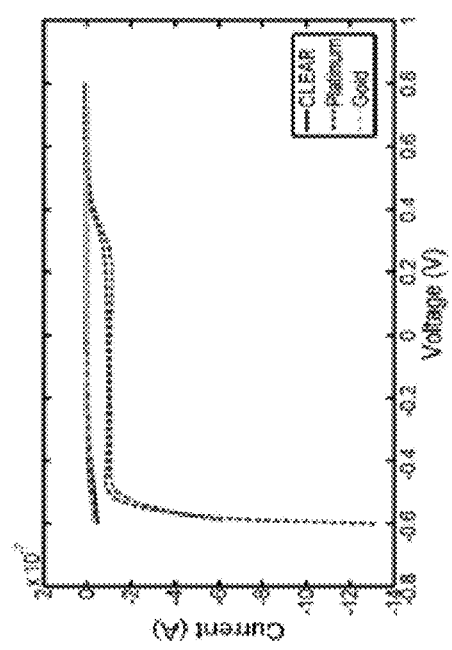

In addition to impedance spectroscopy, cyclic voltammetry was performed on select CLEAR devices, and on devices with gold electrode sites, for comparison purposes. Cyclic voltammetry (CV) was also performed using the Autolab system. CV scans were taken from −0.6 V to 0.8 V with a step potential of 0.0105 V and a scan rate of 0.0500 V/s. The voltage range was chosen so as to stay within the water window. Average CV curves for gold, platinum, and CLEAR devices are shown in FIGS. 6A and 6B. The CV results for the platinum device were different than those for either the gold or the CLEAR devices. The average CV curves for the CLEAR and gold electrode sites were similar. As gold has proven itself as a reliable material for recording electrode sites, this indicates that the graphene conductors will also be sufficient.

Figure 7:
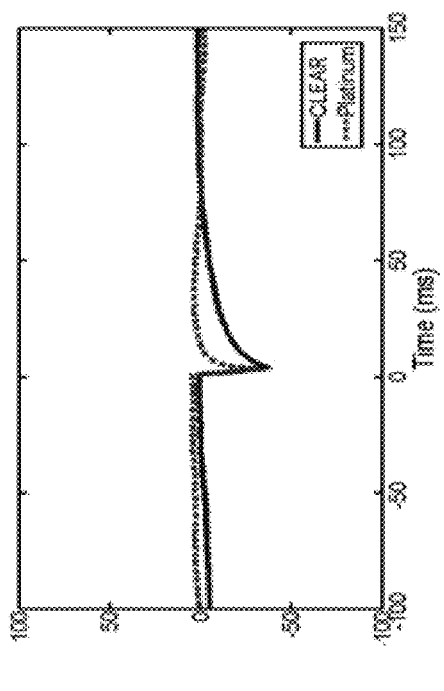
FIG. 7 is a graph of the electrical pulses elicited by the electrode sites for a CLEAR device and by the platinum electrode sites of a traditional micro-ECoG device.

However, if the magnitude of the artifact produced by shining light through the graphene electrode sites is too large, it would be difficult to distinguish optically evoked neural signals from stimulus artifacts, and thus the device would not be useful for optogenetic applications. For this purpose, the photovoltaic effect of the graphene electrode sites was tested to verify that the CLEAR devices are suitable for optogenetic experiments. To test photovoltaic or other photochemical effects, the devices were placed face-down in saline solution and an optical fiber connected to a 100 mW, 473 nm diode LASER (Laserglow Technologies, Ontario, Canada), was used to shine light onto the backs of the electrode sites. The light pulses were delivered by applying 3 V to the LASER for 3 ms (up to 80 mW/mm$^2$) FIG. 7 shows the electrical pulses elicited by the light impingent on graphene and platinum sites. From the plot, it appears that the magnitude of the photovoltaic effect is similar for both the graphene and the platinum sites, although the platinum electrode returns to baseline more quickly. In both cases, the stimulus artifact is less than 50 µV. Since cortical evoked potentials are generally in the range of 100 µV, this should not create a problem in an in vivo setting.

Figure 8:
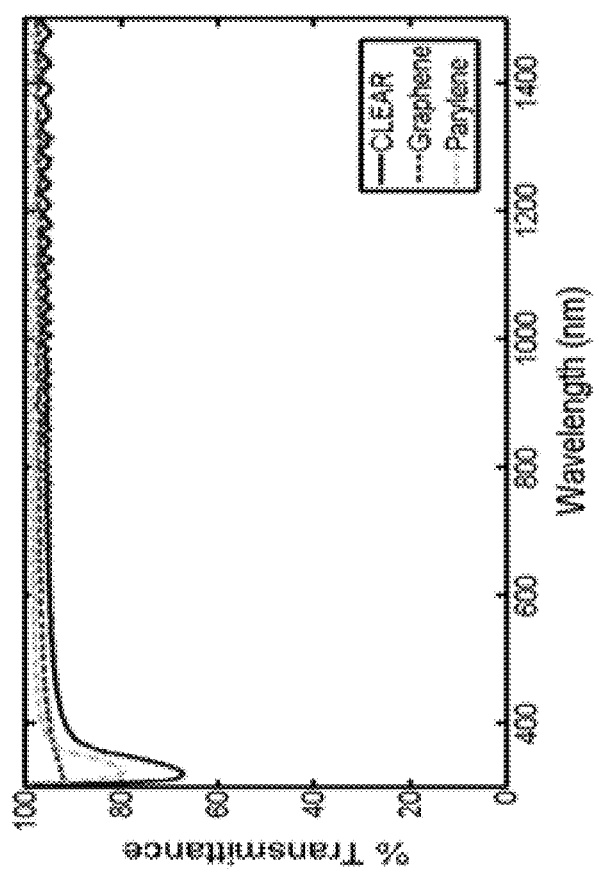
FIG. 8 is a graph of the light transmittance through a sample of four graphene monolayers on a parylene substrate as a function of wavelength.

Another important characteristic for optogenetic application of the CLEAR device is the amount of light transmitted through the graphene electrode sites and parylene substrate. Since the transparent device is intended to both image and project light onto the underlying brain tissue, it is important that a large percentage of the light impingent on the array is transmitted through the device. A plot of the light transmittance through a sample of 4 graphene monolayers on a parylene substrate versus wavelength is shown in FIG. 8. The measurements were taken for light wavelengths from 300 to 1500 nm using a UV/Vis Spectrometer (Perkin Elmer). The sinusoidal shape of the transmittance curve is common for the parylene C material. An average of about 90% of the light impingent on the substrate is transmitted at the desired wavelengths (470 nm for excitation of channelrhodopsin and 570 nm for halorhodopsin). It is noted that the light transmittance through the CLEAR devices is far superior in the UV and IR ranges than reported ITO transmittance values. (See, Granqvist, C. G. & Hultåker, A. Transparent and conducting ITO films: new developments and applications. *Thin Solid Films* 411, 1-5 (2002).)

To demonstrate in vivo performance of the CLEAR devices, the arrays were implanted in two rats and two mice, one wild-type for imaging and one Thy1::ChR2 (Jackson Labs, 012350) for optogenetic testing. Table 1 describes the type of implantation performed in each case and the type of data collected from each animal.

TABLE 1

Summary of implantation schemes and experimental paradigms for each animal. R1 and R2 represent the rats and M1 and M2 represent the mice.

| Animal | Implant Description | In Vivo Vascular Imaging | Impedance Spectroscopy | Baseline Signal Recordings | Electrical Evoked Potentials | Optogenetic Experiments | OCT |
|---|---|---|---|---|---|---|---|
| R1 | Bilateral Rat Pt micro-ECoG and CLEAR device with gold traces | X | X | X | X | | |
| R2 | Rat CLEAR device | | X | X | X | | |
| M1 | Completely Transparent Mouse CLEAR device (terminal) | | | X | | X | |
| M2 | Completely Transparent Mouse CLEAR device (terminal) | X | | | | | X |

All animal procedures were approved by the Institutional Animal Care and Use Committee (IACUC) at the University of Wisconsin-Madison. Surgical procedures and in vivo imaging sessions were performed under anesthesia, and all efforts were made to minimize animal discomfort.

Following implantation of the devices, electrode site impedance spectra and baseline signal recordings were tested daily for the duration of the implantation period in the rats. Electrode site impedance spectra were generated using the Autolab PGSTAT12 described above. Baseline signal recordings were obtained using a TDT neurophysiology work system. Signals were recorded via a 32-channel active TDT headstage, plugged into the PCB connector. The headstage was connected to a TDT PZ2 amplifier, which amplified the signal before sending it to the TDT RZ2 system, from which it was sent to the computer. Five minutes of baseline signal data were recorded during each session. Animals were awake and behaving for the baseline signal recordings and impedance spectra collection.

Figure 9:
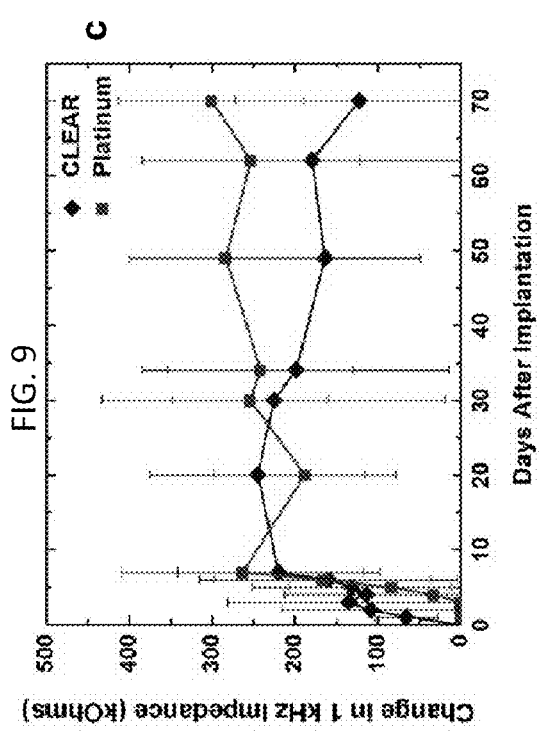
FIG. 9 is a graph of the average electrode site impedance for a CLEAR device and platinum-based micro-ECoG arrays implanted in the same animal as a function of time.

Average electrode site impedance changes (measured from the first day of device implantation) for CLEAR and platinum micro-ECoG arrays implanted in the same animal are plotted over time in FIG. 9. Both devices experienced a steep rise in impedance within the first 10 days after implantation, most likely due to the initial tissue response to the implanted arrays. After this initial sharp increase, the impedances appear to have plateaued, with some minor day-to-day fluctuations. The shape of these impedance curves is characteristic of epidurally implanted micro-ECoG devices. (See, Schendel, A. A. et al. A cranial window imaging method for monitoring vascular growth around chronically implanted micro-ECoG devices. *J. Neurosci. Methods* 218, 121-130 (2013).) There was no statistically significant difference between the impedance changes for the CLEAR and platinum micro-ECoG devices over the entire implantation period, suggesting that the CLEAR device will perform as well as the platinum device over the explored time period.

Figure 10:
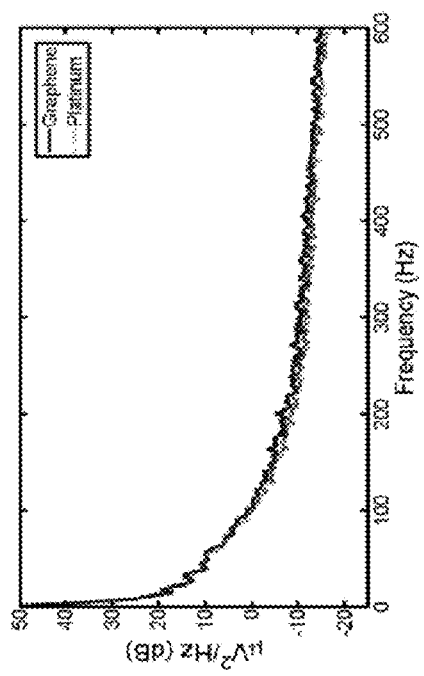
FIG. 10 is a graph of power spectra for the baseline local field potentials recorded by single channels on a CLEAR device and platinum-based micro-ECoG devices.

FIG. 10 shows power spectra for the baseline local field potentials recorded by single channels on the CLEAR and platinum micro-ECoG devices. As with the longitudinal impedance data, there is little difference between the signals recorded by the two different arrays.

Figure 11:
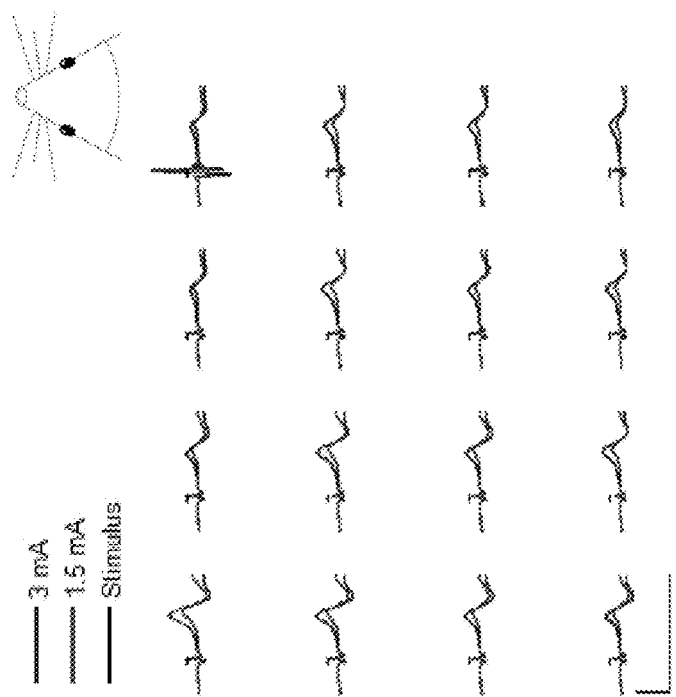
FIG. 11 provides a summary of the evoked potential results for a CLEAR device at two stimulation levels.

In addition to baseline signal recordings and impedance spectroscopy measurements, both rats were tested for electrical evoked potentials. In these experiments, the hindlimbs of the animals were stimulated with surface electrodes placed above and below the sciatic nerve. Stimuli consisted of 1 ms biphasic electrical pulses, with amplitudes varying from 1-3 mA. Evoked potentials were recorded with stimuli applied both ipsilateral and contralateral to the implanted devices, to verify that the result was, in fact, the somatosensory response to the electrical stimulus. If this was true, evoked potentials would be seen only when the stimuli were applied contralateral to the implanted electrode array, due to the crossing of the neural pathways in the brainstem and spinal cord. FIG. 11 shows a summary of the evoked potential results for the CLEAR device at two stimulation levels. In general, the results displayed in FIG. 11 show that the graphene electrode sites are capable of recording both spontaneous baseline activity and evoked neural signals with the same level of clarity as the platinum sites, and generally similar impedance behavior and stability over time.

Figure 12:
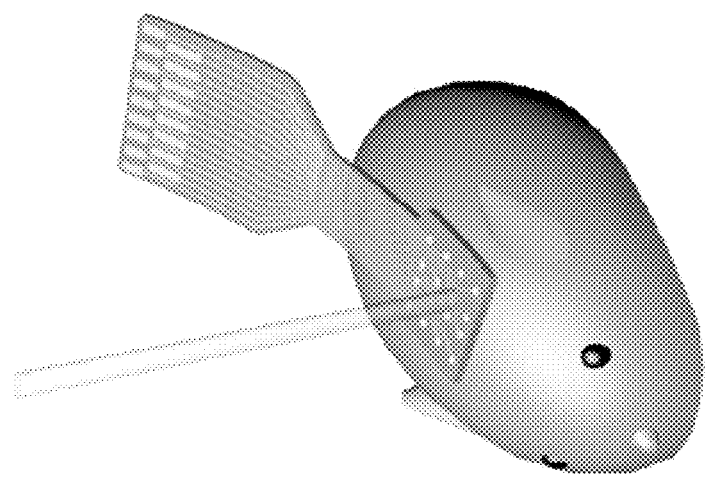
FIG. 12 is a schematic illustration of a mouse implanted with a CLEAR device for the purposes of optogenetic evaluation.

One Thy1::ChR2 mouse was implanted with a CLEAR device for the purposes of optogenetic evaluation. This mouse had neurons expressing the channelrhodopsin-2 protein, making them susceptible to excitation when in contact with blue (473 nm) light. The electrode was implanted on the cortex via the previously described procedure, but in this case, no window was placed over the array. Instead, the brain was left open and an optical fiber attached to the LASER was brought into close proximity with the cortex (FIG. 12).

The anesthesia was switched from isoflurane, which inhibits neural signaling, to a combination of ketamine (75 mg/kg) and dexmedetomidine (25 µg/kg). Concentrated blue light, with a maximum power of 80 mW/mm$^2$, was then directed onto various regions of the brain, through the CLEAR device, while simultaneously recording the neural response to the optical stimulation. The average evoked response is shown for three different stimulation levels in FIG. 13. The initial peak is the stimulus artifact resulting from the photovoltaic effect, and the second, longer peak is the evoked neural response. The evoked response is clearly distinguishable from the stimulus artifact, suggesting that the CLEAR device is a suitable technology for optogenetic experiments.

Figure 13:
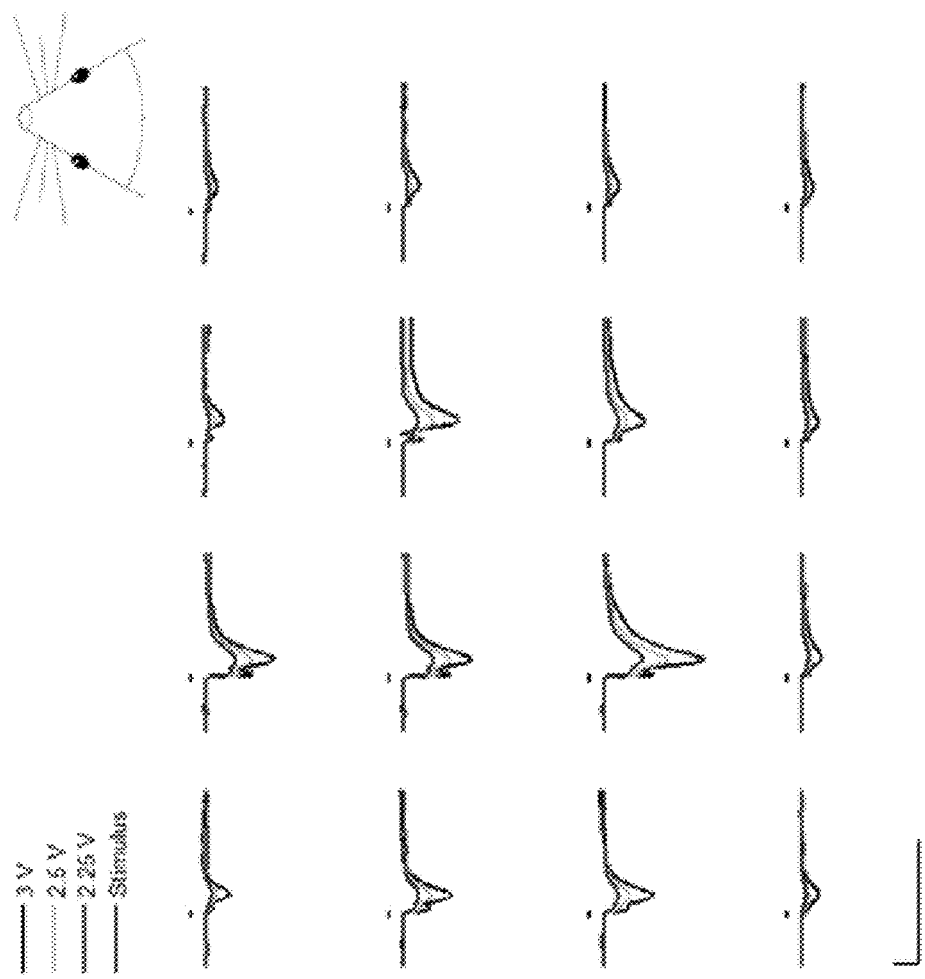
FIG. 13 shows the average evoked response recorded by a CLEAR device for three different stimulation levels.

Once experimentation was complete, the animal was euthanized with an intraperitoneal injection of Fatal PLUS pentobarbitol solution, and a control experiment was conducted with the electrode on the brain of the euthanized animal, to verify that the signals recorded were from neurons affected by the light stimulation, and not due to the photovoltaic artifact. The signal magnitude was significantly lower for the recordings obtained from the post-mortem control experiment than for the signals recorded from the living animal. Furthermore, for the control, there was only an evoked signal on the channels which experienced direct light stimulation, whereas FIG. 13 shows a large spatial distribution of the signals from the live animal. These results demonstrate that the signals in FIG. 13 were evoked neural responses to the light stimulation, while those from the euthanized animal were a result of the photovoltaic artifact.

Figure 14A:
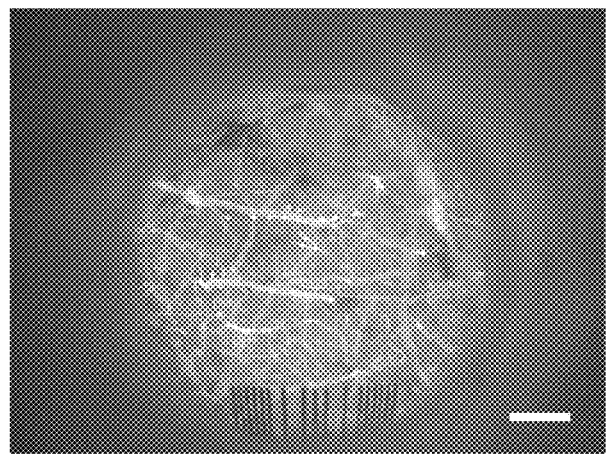
FIG. 14A is a fluorescent images of cortical vasculature through a CLEAR micro-ECoG device; 14B is a higher magnification image of the fluorescent image in 14A; 14C shows a fluorescent image of a rat-sized micro-ECoG array using platinum electrode sites. The scale bars in A and B represent 250 µm. The scale bar in C represents 750 µm.
Figure 14B:
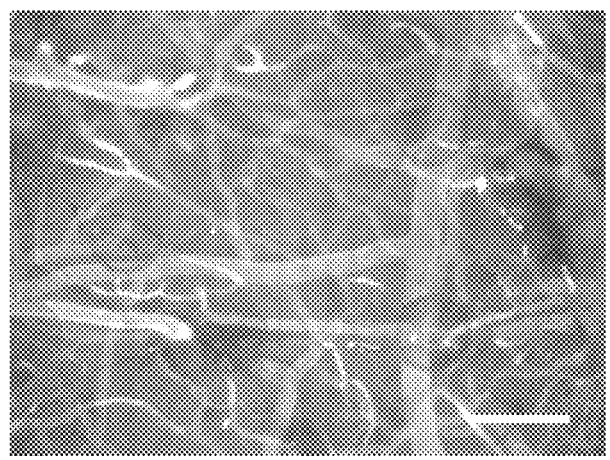
Figure 14C:
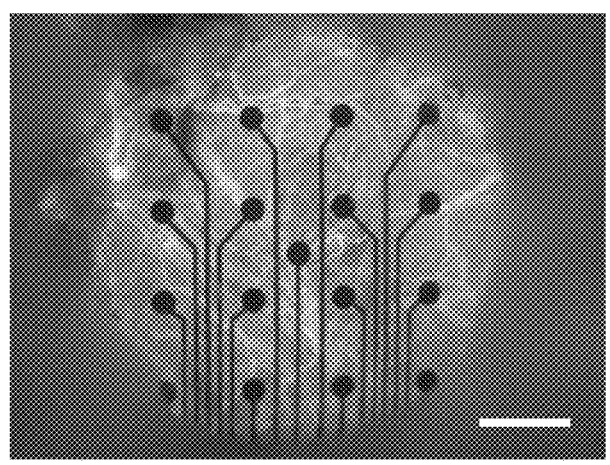

A subset of the implanted animals was imaged via the cranial window imaging method previously described by Schendel et al. (Schendel, A. A. et al. A cranial window imaging method for monitoring vascular growth around chronically implanted micro-ECoG devices. *J. Neurosci. Methods* 218, 121-130 (2013).) Images were taken in brightfield and under blue (470 nm) light with the aid of a tail vein injection of FITC-Dextran to fluorescently label the vasculature. Representative fluorescent images of the cortical vasculature through the CLEAR micro-ECoG device are shown in FIGS. 14A and B. These images demonstrate the clarity of the graphene electrode sites and the ability to view the underlying cortex and cerebral vasculature through the CLEAR device. FIG. 14C shows cranial window images of a platinum micro-ECoG array, with the electrode sites and traces clearly visible.

Figure 15B:
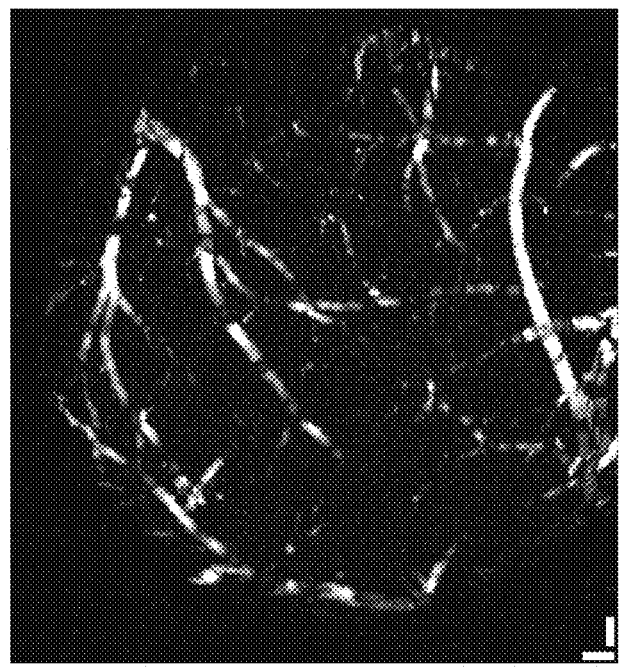
FIG. 15B. is a Doppler blood flow image showing the directionality of blood flowing through the vasculature through the device. Scale bars represent 100 µm.
Figure 15A:
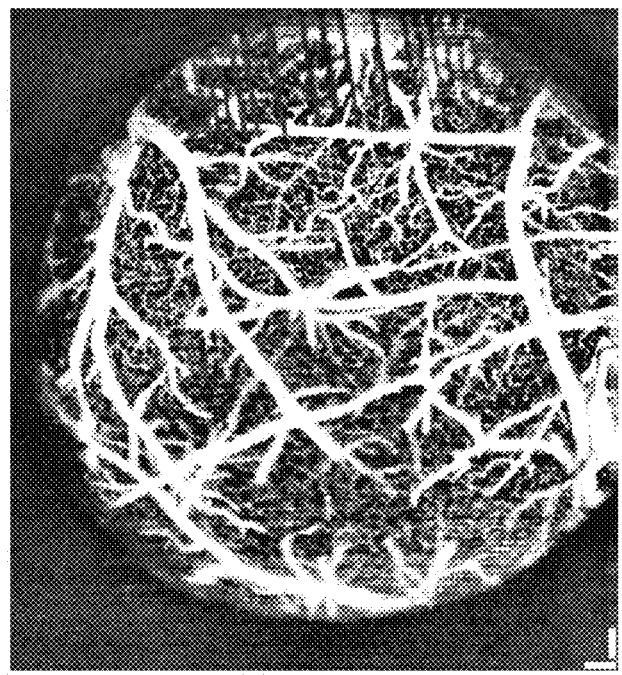
FIG. 15A is a three-dimensional OCT showing cortical vasculature visible through a CLEAR device.

In addition to fluorescence imaging of the cortical vasculature, optical coherence tomography (OCT) demonstrates the ability of the CLEAR device based on its high transparency in the IR spectral range. The structure of the cerebral vasculature can be captured as a 3D OCT angiogram through the device, as shown in FIG. 15A. (See, Srinivasan, V. J. et al. Rapid volumetric angiography of cortical microvasculature with optical coherence tomography. *Opt. Lett.* 35, 43-45 (2010).) Furthermore, a velocity profile of the blood flow below the CLEAR device was demonstrated. (See, Wang, R. K. & An, L. Doppler optical micro-angiography for volumetric imaging of vascular perfusion in vivo. *Opt. Express* 17, 8926-8940 (2009).) A Doppler blood flow image showing the directionality of blood flowing through the vasculature is shown in FIG. 15B. In both images dark lines produced by the gold traces were visible on the right side, however the graphene electrodes produced no dark patterns at the center of image. It is important to note that OCT utilizes infrared light wavelengths, which may create artifacts with ITO-based devices, depending on the fabrication process.

The results of this study demonstrate that the CLEAR micro-ECoG device is capable of recording neural signals with the same degree of clarity as the platinum array, and a comparable longitudinal tissue response. Unlike the platinum array, the CLEAR device allows for optogenetic stimulation and both fluorescence and OCT imaging directly through the electrode sites, due to the broad spectrum transparency of graphene.

Example 2

This example illustrates a method of forming wrinkled graphene for use in an electrode site of an electrocorticography device.

Figure 16:
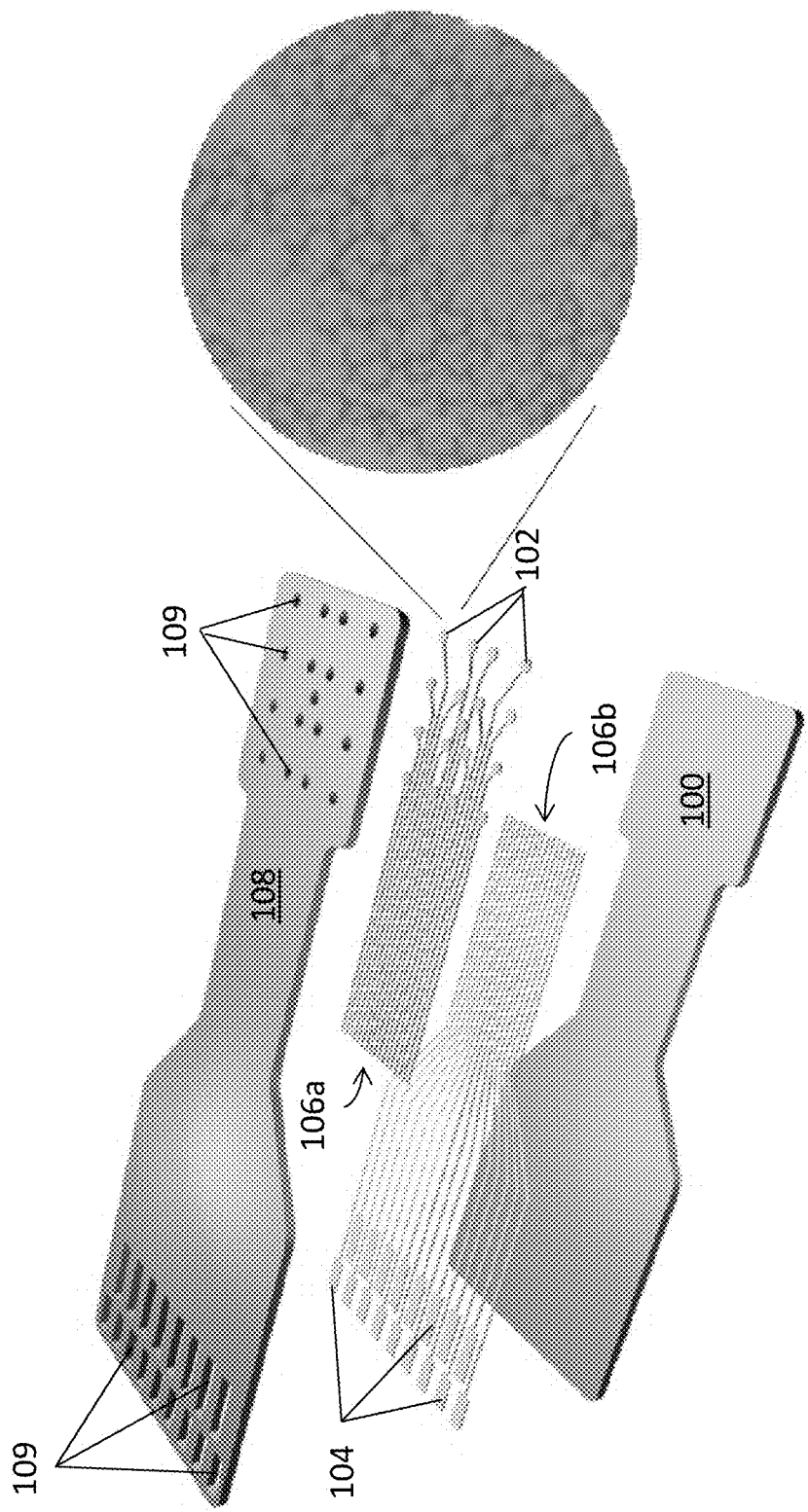
FIG. 16 is an embodiment of an electrophysiology device with an SEM image of wrinkled graphene in the electrode site.

Graphene was grown on a copper foil and then one side of the foil was spin coated with PMMA. The sample with the PMMA protection layer was floated in a ferro chloride (FeCl$_3$) solution to selectively remove the copper. The remaining graphene was rinsed in water. The sample was then placed onto a substrate (e.g., SiO$_2$, Parylene C, etc.) and allowed to dry in nitrogen ambient for longer than one hour. The PMMA was then removed through a standard cleaning procedure using acetone, isopropyl alcohol (IPA), and DI water. A layer of silicon oxide (SiO$_2$), with a thickness of 20 nm, was deposited using e-beam evaporator to protect the graphene. Unsaturated silicon nitride (SiNx) was deposited as the straining material using PECVD (Plasma Enhanced Chemical Vapor Deposition). The detailed SiNx deposition recipe was as follow: N$_2$O 1010 sccm, SiH$_4$ 150 sccm, NH$_3$ 50 sccm, RF 46 W, Pressure 950 mT, Temp. 350° C., Time 120 sec for thickness: 32 nm (Unaxis 790 RIE etcher). The image of wrinkled graphene provided in FIG. 16 was taken 36 hours after SiNx deposition, as it takes some time for the materials to get strained. The images were taken by an optical microscope (Nikon LV100) and LEO 1530 SEM (scanning electron microscope).

Additional descriptions of methods for depositing silicon nitride stressor materials via PECVD can be found in Parsons et al., *J. Appl. Phys.*, 70, 1553 (1991) and Mackenzie et al., 207$^{th}$ Electrochem. Soc. Meeting, invited paper (2005).

Graphene sheets having one or more wrinkled portions and one or more planar (non-wrinkled) portions can be fabricated by selectively patterning the stressor material on the graphene.

The word "illustrative" is used herein to mean serving as an example, instance, or illustration. Any aspect or design described herein as "illustrative" is not necessarily to be construed as preferred or advantageous over other aspects or designs. Further, for the purposes of this disclosure and unless otherwise specified, "a" or "an" can mean "one or more".

The foregoing description of illustrative embodiments of the invention has been presented for purposes of illustration and of description. It is not intended to be exhaustive or to limit the invention to the precise form disclosed, and modifications and variations are possible in light of the above teachings or may be acquired from practice of the invention. The embodiments were chosen and described in order to explain the principles of the invention and as practical applications of the invention to enable one skilled in the art to utilize the invention in various embodiments and with various modifications as suited to the particular use contemplated. It is intended that the scope of the invention be defined by the claims appended hereto and their equivalents.

What is claimed is:

1. A device for detecting electrical activity in electrically active biological tissue, the device comprising:
   a micro-electrode array configured for implantation on the electrically active biological tissue and comprising:
   a biocompatible, dielectric substrate;
   a plurality of electrode sites on the biocompatible, dielectric substrate, the electrode sites comprising one or more sheets of electrically conductive graphene, wherein the one or more sheets of electrically conductive graphene are non-planar sheets, and further wherein the non-planar sheets of graphene comprise wrinkled graphene or crumpled graphene;
   a plurality of electrically conductive contacts on the biocompatible, dielectric substrate; and
   electrically conductive interconnects connecting the electrode sites to the contacts;
   wherein the electrode sites and the portion of the substrate on which the electrode sites are disposed are transparent in at least a portion of the wavelength range from about 300 to about 2000 nm.

2. The device of claim 1, wherein the substrate is a mechanically flexible polymeric substrate.

3. The device of claim 2, wherein the substrate comprises a shape memory polymer.

4. The device of claim 1, wherein the number of electrically conductive sheets of graphene in the electrode sites is in the range from 1 to 10.

5. The device of claim 1, wherein the electrically active biological tissue is neural tissue and the device further comprises an electronic device electrically connected to the contacts that is configured to receive neural signals recorded at the electrode sites and to amplify, display, store or analyze the neural signals.

6. The device of claim 1, wherein the graphene around the perimeters of the electrode sites comprises wrinkled graphene or crumpled graphene and the graphene in the center regions of the electrode sites comprises planar graphene.

7. A method of detecting electrical signals in electrically active biological tissue using the device of claim 1, the method comprising:
   implanting the micro-electrode array on the electrically active biological tissue; and
   recording an electrical signal generated in the electrically active biological tissue at the electrode sites.

8. The method of claim 7, wherein the tissue is muscle tissue.

9. The method of claim 7, wherein the tissue is cardiac tissue.

10. The method of claim 7, wherein the tissue is neural tissue.

11. The method of claim 10, wherein the electrical signal is a neural response generated by neural cells in the neural tissue, the method further comprising exposing the neural tissue to a sensory stimulus to evoke the neural response.

12. The method of claim 11, wherein the neural cells incorporate light-sensitive proteins and the sensory stimulus comprises light directed onto the neural tissue through the electrode sites, the light comprising wavelengths that photostimulate the light-sensitive proteins.

13. The method of claim 11, wherein the neural tissue is fluorescently labeled, the method further comprising directing ultraviolet light onto the neural tissue through the electrode sites to induce the emission of fluorescence from the fluorescently labeled tissue and recording the emitted fluorescence.

14. The method of claim 11, wherein the neural tissue is the surface of a cerebral cortex.

15. The method of claim 14, further comprising exposing the cerebral cortex to a sensory stimulus to evoke the generation of action potentials, wherein the action potentials are the neural response.

16. The method of claim 15, wherein the neural cells incorporate light-sensitive proteins and the sensory stimulus comprises light directed onto the surface of the cerebral cortex through the electrode sites, the light comprising wavelengths that photostimulate the light-sensitive proteins.

17. The method of claim 14, wherein the cerebral cortex comprises fluorescently labeled tissue, the method further comprising directing ultraviolet light onto the cerebral cortex through the electrode sites to induce the emission of fluorescence from the fluorescently labeled tissue and recording the emitted fluorescence.

18. The method of claim 14, further comprising directing infrared light onto the cerebral cortex through the electrode sites and recording backscattered light from the cerebral cortex.

19. A method of detecting backscattered light from neural tissue using the device of claim 1,
   the method comprising:
   implanting the micro-electrode array on the neural tissue; and
   directing infrared light onto the neural tissue through the electrode sites and recording backscattered light from the neural tissue.

20. The method of claim 19, wherein the infrared light directed onto the neural tissue through the electrode sites comprises wavelengths in the range from 1300 nm to 2000 nm.

* * * * *